US009055862B2

(12) United States Patent
Watanabe et al.

(10) Patent No.: US 9,055,862 B2
(45) Date of Patent: Jun. 16, 2015

(54) IMAGE PROCESSING DEVICE AND IMAGE PROCESSING METHOD (71) Applicant: Olympus Corporation, Tokyo (JP)

(72) Inventors: Toshiaki Watanabe, Tokyo (JP); Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 379 days.

(21) Appl. No.: 13/727,164

(22) Filed: Dec. 26, 2012

(65) Prior Publication Data
US 2013/0113908 A1 May 9, 2013

Related U.S. Application Data (63) Continuation of application No. PCT/JP2011/064671, filed on Jun. 27, 2011.

(30) Foreign Application Priority Data

Jul. 2, 2010 (JP) .................................. 2010-152210

(51) Int. Cl.
*H04N 7/18* (2006.01)
*A61B 1/00* (2006.01)
(Continued)

(52) U.S. Cl.
CPC ............ *A61B 1/00009* (2013.01); *A61B 1/043* (2013.01); *A61B 1/0638* (2013.01); *A61B 1/0646* (2013.01); *G02B 23/2461* (2013.01); *G02B 23/2484* (2013.01)

(58) Field of Classification Search
CPC ...... A61B 1/26; A61B 1/00091; A61B 1/127; A61B 1/12; A61B 1/00135; A61B 1/05; A61B 1/042; H04N 2005/2255; H04N 9/045; H04N 5/2256
USPC ............................................ 348/70; 600/157
See application file for complete search history.

(56) References Cited

U.S. PATENT DOCUMENTS 5,590,660 A 1/1997 MacAulay et al.
2006/0025692 A1 2/2006 Ishihara
(Continued)

FOREIGN PATENT DOCUMENTS

EP 1 829 473 A2 9/2007
JP 2001-258829 A 9/2001
(Continued)

OTHER PUBLICATIONS

Extended European Supplementary Search Report dated Oct. 21, 2014 from related European Application No. 11 80 0784.8.
(Continued)

*Primary Examiner* — Sath V Perungavoor
*Assistant Examiner* — Howard D Brown, Jr.
(74) *Attorney, Agent, or Firm* — Scully, Scott, Murphy & Presser, PC (57) ABSTRACT Provided is an image processing device including an illuminating portion that irradiates a subject with illumination light and excitation light; a fluorescence image-acquisition portion that acquires a fluorescence image by capturing fluorescence generated at the subject; a return-light image-acquisition portion that acquires a return-light image by capturing return light returning from the subject; a color-image generating portion that generates a plurality of color images by adding different types of color information that constitute a color space to the acquired fluorescence image and return-light image; and an image combining portion that combines the plurality of color images that have been generated, wherein at least one of the fluorescence image and the return-light image is subjected to, by the color-image generating portion), correction processing in which exponents for distance characteristics, which are approximated to exponential functions, for the fluorescence image and the return-light image are matched with each other.

9 Claims, 9 Drawing Sheets (51) Int. Cl.
*A61B 1/04* (2006.01)
*G02B 23/24* (2006.01)
*A61B 1/12* (2006.01)
*A61B 1/06* (2006.01)

(56) References Cited

U.S. PATENT DOCUMENTS

| | | | | |
|---|---|---|---|---|
| 2006/0161047 | A1* | 7/2006 | Miyoshi | 600/157 |
| 2007/0260119 | A1* | 11/2007 | Otawara | 600/129 |
| 2007/0276259 | A1 | 11/2007 | Okawa et al. | |
| 2008/0064928 | A1* | 3/2008 | Otawara | 600/129 |
| 2008/0167529 | A1* | 7/2008 | Otawara | 600/168 |
| 2011/0121200 | A1* | 5/2011 | Watanabe | 250/458.1 |
| 2011/0267493 | A1* | 11/2011 | Kubo et al. | 348/223.1 |
| 2012/0302893 | A1* | 11/2012 | Ishihara | 600/478 |
| 2012/0328175 | A1* | 12/2012 | Watanabe | 382/132 |
| 2013/0039562 | A1* | 2/2013 | Watanabe | 382/132 |
| 2013/0235258 | A1* | 9/2013 | Shida | 348/370 |
| 2013/0250079 | A1* | 9/2013 | Nakamura et al. | 348/68 |

FOREIGN PATENT DOCUMENTS

| | | |
|---|---|---|
| JP | 3309276 B | 7/2002 |
| JP | 2003-24268 A | 1/2003 |
| JP | 2006-122234 A | 5/2006 |
| JP | 2006-263044 | 10/2006 |
| JP | 2007-313169 | 12/2007 |

OTHER PUBLICATIONS

English Language Abstract Only of Japanese Publication No. 2000-270265 A, dated Sep. 29, 2000(corresponding to JP 3309276 B).
English Language Abstract Only of corresponding Japanese Publication No. JP 2004-229590 A dated Aug. 19, 2004 (corresponding to JP 2003-24268A).
International Search Report dated Aug. 9, 2011 issued in PCT/JP2011/064671.

* cited by examiner

IMAGE PROCESSING DEVICE AND IMAGE PROCESSING METHOD

CROSS-REFERENCE TO RELATED APPLICATIONS

This is a continuation of International Application PCT/JP2011/064671, with an international filing date of Jun. 27, 2011, which is hereby incorporated by reference herein in its entirety. This application claims the benefit of Japanese Patent Application No. 2010-152210, the contents of which are incorporated herein by reference.

TECHNICAL FIELD

The present invention relates to an image processing device and an image processing method.

BACKGROUND ART

In the related art, there is a known image processing device in which a fluorescence image and a reflected-light image acquired from the same subject are combined to be displayed on the same screen by assigning different display colors thereto (for example, see Patent Literature 1). In other words, depending on the difference in brightness between the fluorescence image and the reflected-light image, a region in which the fluorescence has a relatively greater brightness is displayed with a different color from a region in which the reflected light has a relatively greater brightness, and thus, a fluorescent region with a greater brightness is displayed conspicuously.

CITATION LIST

Patent Literature

{PTL 1} U.S. Patent Application Publication No. 5590660

SPECIFICATION

Summary of Invention

A first aspect of the present invention provides an image processing device including an illuminating portion that irradiates a subject with illumination light and excitation light; a fluorescence image-acquisition portion that acquires a fluorescence image by capturing fluorescence generated at the subject due to the irradiation with the excitation light from the illuminating portion; a return-light image-acquisition portion that acquires a return-light image by capturing return light returning from the subject due to the irradiation with the illumination light from the illuminating portion; a color-image generating portion that generates a plurality of color images by adding different types of color information that constitute a color space to the fluorescence image acquired by the fluorescence image-acquisition portion and the return-light image acquired by the return-light image-acquisition portion; and an image combining portion that combines the plurality of color images generated by the color-image generating portion, wherein at least one of the fluorescence image and the return-light image is subjected to, by the color-image generating portion, correction processing in which exponents for distance characteristics, which are approximated to exponential functions, for the fluorescence image and the return-light image are matched with each other.

With the first aspect of the present invention, by irradiating the subject with the illumination light emitted from the illuminating portion, the return-light image is acquired by capturing the return light from the subject by means of the return-light image-acquisition portion, and, by irradiating the subject with the excitation light from the illuminating portion, the fluorescence image is acquired by capturing the fluorescence generated at the subject by means of the fluorescence image-acquisition portion. At the color-image generating portion, different types of color information are added to the acquired return-light image and fluorescence image, and thus, the plurality of color images are generated. Here, the generation of the plurality of color images by adding different types of color information that constitute the color space refers to, for example, assignment of the fluorescence image or the return-light image to the respective types of information about R, G, and B dimensions that constitute an RGB color space. The plurality of color images that have been generated are input to the image combining portion to be combined.

In the first aspect of the present invention, an R-component, a G-component, and a B-component may constitute the color information.

In addition, with the first aspect of the present invention, the color-image generating portion may raise a gradation value of the return-light image to the power of a third exponent that is obtained by dividing a first exponent obtained by means of a power approximation for the distance characteristic of the fluorescence image by a second exponent obtained by means of a power approximation for the distance characteristic of the return-light image.

Here, the distance characteristic of the fluorescence image and the distance characteristic of the return-light image respectively mean the characteristic regarding the amount of the fluorescent light that is received depending on the distance to the image-acquisition portion from the subject emitting light due to the excitation light and the characteristic regarding the amount of the return light that is received depending on the distance to the image-acquisition portion from the subject illuminated by the illumination light.

In addition, with the first aspect of the present invention, the color-image generating portion may raise a gradation value of the fluorescence image to the power of a fourth exponent that is obtained by dividing a second exponent obtained by means of a power approximation for the distance characteristic of the return-light image by a first exponent obtained by means of a power approximation for the distance characteristic of the fluorescence image.

Furthermore, with the first aspect of the present invention, the color-image generating portion may raise a gradation value of the fluorescence image to the power of the inverse of a first exponent obtained by means of a power approximation for the distance characteristic of the fluorescence image and also raise a gradation value of the return-light image to the power of the inverse of a second exponent obtained by means of a power approximation for the distance characteristic of the return-light image.

In addition, with the first aspect of the present invention, the color-image generating portion may raise a gradation value of the return-light image to the power of a fifth exponent such that identical values are obtained when gradation values of the fluorescence image are divided by values obtained by raising gradation values of the return-light images acquired at different distances to the power of the fifth exponent.

Furthermore, a second aspect of the present invention provides an image processing method including: inputting a fluorescence image obtained by capturing fluorescence generated at a subject due to irradiation with excitation light and a return-light image obtained by capturing return light returning from the subject due to irradiation with illumination light; applying correction processing by raising a gradation value of the return-light image to the power of a third exponent that is obtained by dividing a first exponent obtained by means of a power approximation for a distance characteristic of the fluorescence image by a second exponent obtained by means of a power approximation for a distance characteristic of the return-light image; generating a plurality of color images by adding different types of color information that constitute a color space to the fluorescence image and the return-light image; and combining the plurality of color images that have been subjected to the correction processing.

Additionally, a third aspect of the present invention provides an image processing method including: inputting a fluorescence image obtained by capturing fluorescence generated at a subject due to irradiation with excitation light and a return-light image obtained by capturing return light returning from the subject due to irradiation with illumination light; applying correction processing by raising a gradation value of the fluorescence image to the power of a fourth exponent that is obtained by dividing a second exponent obtained by means of a power approximation for a distance characteristic of the return-light image by a first exponent obtained by means of a power approximation for a distance characteristic of the fluorescence image; generating a plurality of color images by adding different types of color information that constitute a color space to the fluorescence image and the return-light image; and combining the plurality of color images that have been subjected to the correction processing.

Furthermore, a fourth aspect of the present invention provides an image processing method including: inputting a fluorescence image obtained by capturing fluorescence generated at a subject due to irradiation with excitation light and a return-light image obtained by capturing return light returning from the subject due to irradiation with illumination light; applying correction processing by raising a gradation value of the fluorescence image to the power of the inverse of a first exponent obtained by means of a power approximation for a distance characteristic of the fluorescence image and also by raising a gradation value of the return-light image to the power of the inverse of a second exponent obtained by means of a power approximation for a distance characteristic of the return-light image; generating a plurality of color images by adding different types of color information that constitute a color space to the fluorescence image and the return-light image; and combining the plurality of color images that have been subjected to the correction processing.

DESCRIPTION OF EMBODIMENT

An image processing device and an image processing method according to an embodiment of the present invention will be described below with reference to the drawings.

An image processing device 6 according to this embodiment is provided in an endoscope device 1.

Figure 1:
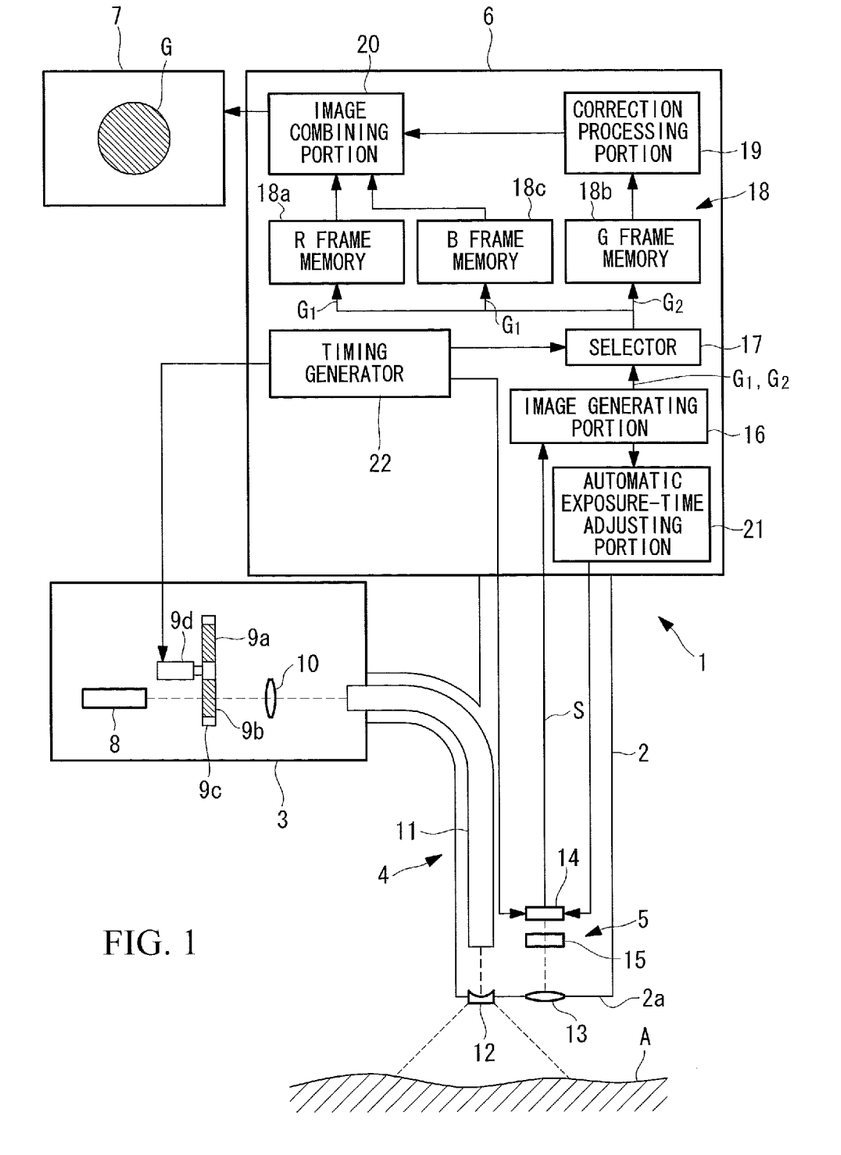
FIG. 1 is an overall configuration diagram showing an endoscope device including an image processing device according to an embodiment of the present invention.

As shown in FIG. 1, the endoscope device 1 is provided with a long, thin inserted portion 2 that is inserted into a body; a light source portion (illuminating portion) 3; an illumination unit (illuminating portion) 4 that radiates illumination light and excitation light from the light source portion 3 toward an observation subject (imaging subject) A from the tip of the inserted portion 2; an image-acquisition unit (fluorescence image-acquisition portion, return-light image-acquisition portion) 5 that is provided at the tip of the inserted portion 2 and that acquires image information of biological tissue, that is, the observation subject A; the image processing device 6 according to this embodiment, which is disposed at the basal side of the inserted portion 2 and that processes the image information acquired by the image-acquisition unit 5; and a monitor 7 that displays an image G processed by the image processing device 6.

The light source portion 3 is provided with a xenon lamp 8; filters 9a and 9b that extract the excitation light (for example, wavelength band of 480 to 500 nm) and the illumination light (for example, wavelength band of 540 to 580 nm) from the radiated light emitted from the xenon lamp 8; and a coupling lens 10 that focuses the excitation light and the illumination light extracted by the filters 9a and 9b.

Figure 2:
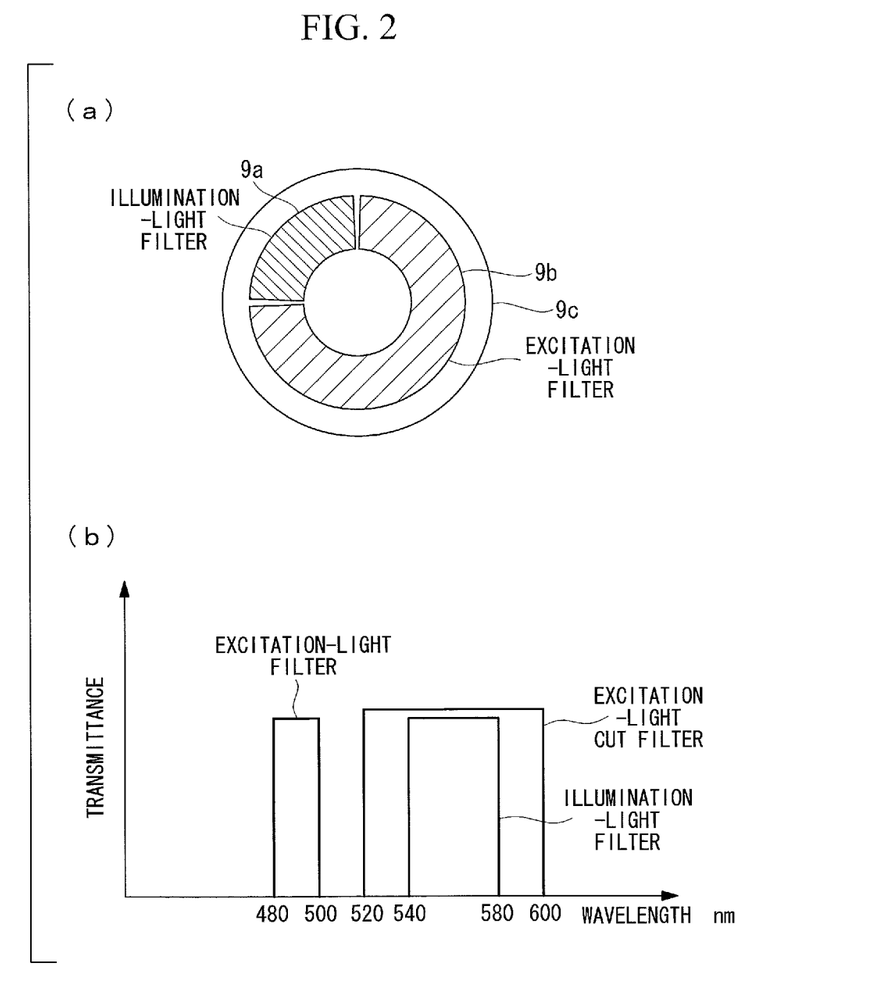
FIG. 2 is a diagram for explaining a filter of the endoscope device in FIG. 1.

The filters 9a and 9b are provided in a turret 9c, such as the one shown in FIG. 2, and are placed in an optical path of the radiated light in an alternating manner by rotating the turret 9c so as to generate the excitation light and the illumination light in a time-division manner.

The illumination unit 4 is disposed in the longitudinal direction of the inserted portion 2 approximately over the entire length thereof and is provided with a light-guide fiber 11 that guides the excitation light and the illumination light that have been focused by the coupling lens 10 and an illumination optical system 12 that is provided at the tip of the inserted portion 2 and that spreads the excitation light and the illumination light guided thereto through the light-guide fiber 11 so as to be radiated onto the observation subject A facing a tip surface 2a of the inserted portion 2.

The image-acquisition unit 5 is provided with an objective lens 13 that collects fluorescence coming from a predetermined observation area in the observation subject A, generated due to irradiation with the excitation light and return light of the illumination light, and an image-acquisition element 14, such as a CCD, that captures the florescence and the return light collected by the objective lens 13. In the figure, reference sign 15 indicates an excitation-light cut filter that blocks the excitation light (allows only the light in the wavelength band of, for example, 520 to 600 nm, to pass therethrough) from the light collected by the objective lens 13.

The image processing device 6 according to this embodiment is provided with an image generating portion 16 that generates a fluorescence image $G_1$ and a return-light image $G_2$ from image signal S acquired by the image-acquisition element 14; a selector 17 that selects one of the images $G_1$ and $G_2$ output from the image generating portion 16; R, G, and B frame memories 18a, 18b, and 18c that separately receive the input fluorescence image $G_1$ and return-light image $G_2$ selected by the selector 17 and add different types of color information thereto; a correction processing portion 19 that applies correction processing to the return-light image $G_2$ output from the G frame memory 18b; and an image combining portion 20 that combines the fluorescence image $G_1$ and the return-light image $G_2$ to which the color information has been added.

A color-image generating portion 18 is formed of the R, G, and B frame memories 18a, 18b, and 18c and the correction processing portion 19.

Reference sign 21 indicates an automatic exposure-time adjusting portion that automatically adjusts the exposure time of the image-acquisition element 14 based on the images $G_1$ and $G_2$ generated by the image generating portion 16, and reference sign 22 indicates a timing generator that synchronizes a motor 9d that drives the turret 9c with the selector 17.

At the timing at which the timing generator 22 gives a command to the motor 9d so that the filter 9a for the illumination light is placed on the optical axis, the selector 17 outputs the return-light image $G_2$, which is output thereto from the image generating portion 16, to the G frame memory 18b based on the command from the timing generator 22, and the selector 17 outputs the fluorescence image $G_1$, which is output thereto at another timing, to the B and R frame memories 18a and 18c.

The correction processing portion 19 raises the gradation value of each pixel in the return-light image $G_2$, which has been output thereto from the G frame memory 18b, to the power of an exponent a. The exponent a is determined as below.

Figure 3:
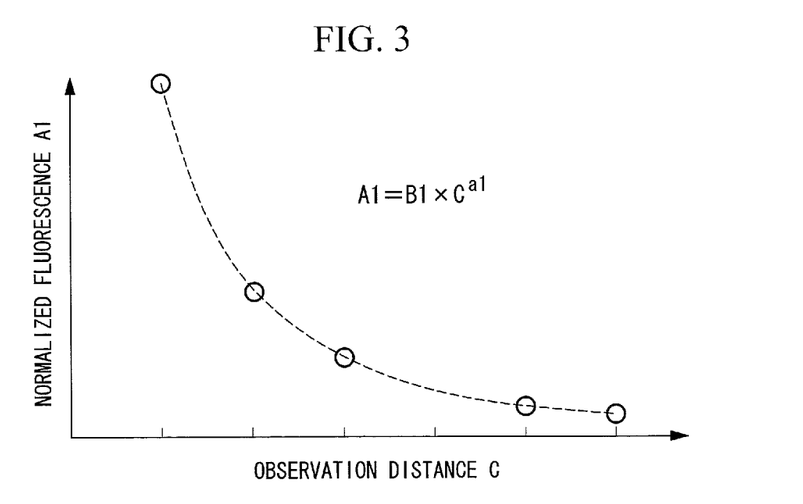
FIG. 3 is a diagram showing a graph of the distance characteristic with respect to gradation values of a fluorescence image, created by using a standard specimen.
Figure 4:
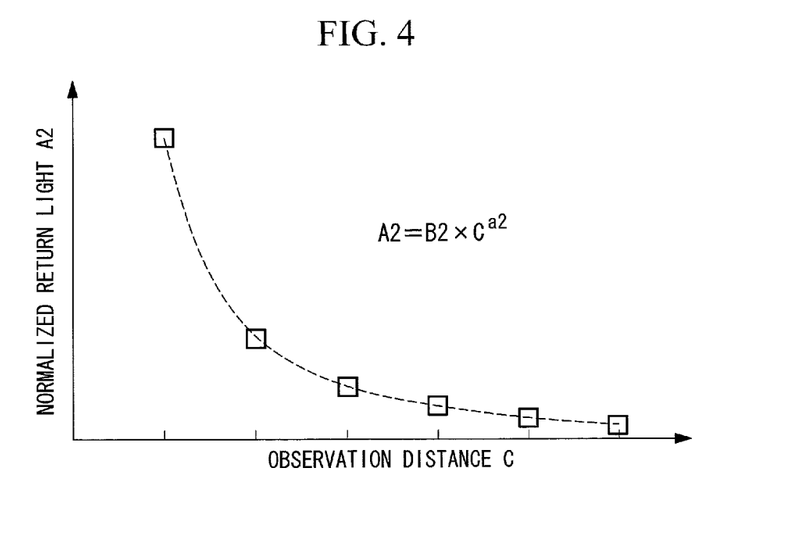
FIG. 4 is a diagram showing a graph of the distance characteristic with respect to gradation values of a return-light image, created by using the standard specimen.

Specifically, the distance characteristic of a normalized fluorescence image $G_1'$ obtained by dividing the fluorescence image $G_1$ acquired by the image-acquisition element 14 by the exposure time and the distance characteristic of a normalized return-light image $G_2'$ obtained by dividing the return-light image $G_2$ by the exposure time are prepared, as shown in FIGS. 3 and 4.

Figure 5:
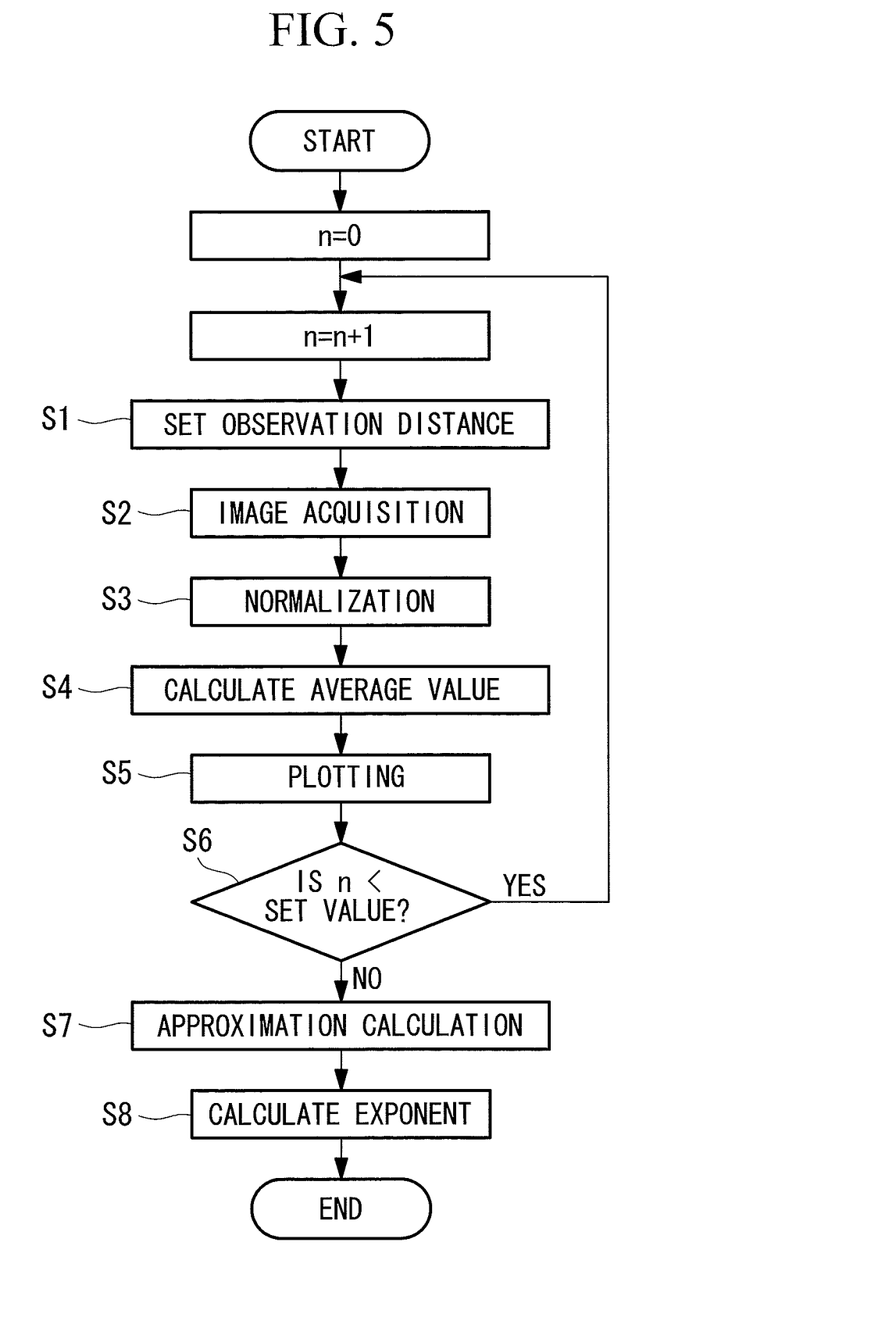
FIG. 5 is a flowchart showing an example procedure for creating the graphs in FIGS. 3 and 4.

As shown in FIG. 5, the distance characteristics of the normalized fluorescence image $G_1'$ and the normalized return-light image $G_2'$ are created by, while changing the distance (observation distance) of the objective lens 13 with respect to a standard specimen having similar optical characteristic to biological tissue containing a fluorescent dye (Step S1), acquiring the fluorescence image $G_1$ and the return-light image $G_2$ (Step S2), performing normalizing computations (Step S3), calculating average values of the gradation values for a region of interest (Step S4), plotting graph (Step S5), and repeating these steps (Step S6).

Then, by performing a power approximation for each of the two created graphs of the distance characteristics (Step S7), the distance characteristic of the normalized fluorescence image $G_1'$ is expressed as an exponential function of the observation distance based on a first exponent a1, as shown in FIG. 3, and the distance characteristic of the normalized return-light image $G_2'$ is expressed as an exponential function of the observation distance based on a second exponent a2, as shown in FIG. 4. By using these exponents a1 and a2, the exponent a used at the correction processing portion 19 is given by a=a1/a2 (Step S8).

A more detailed description will be given below.

With the above-described method, the distance characteristic of the normalized fluorescence image $G_1'$ is determined to be $A1=B1 \times C^{a1}$, and the distance characteristic of the normalized return-light image $G_2'$ is determined to be $A2=B2 \times C^{a2}$.

Here, A1 is the gradation value of the normalized fluorescence image $G_1'$, A2 is the gradation value of the normalized return-light image $G_2'$, B1 and B2 are constants, and C is the observation distance.

Here, the calculation for $$A3 = A2^a \quad (1)$$

will be considered. In Equation (1), A3 is a gradation value of a corrected normalized return-light image $G_2''$.

Equation (1) can be modified as follows:

$$A3 = A2^a = A2^{(a1/a2)} = B2^{(a1/a2)} \times C^{a1} = B2' \times C^{a1}.$$

In other words, by calculating Equation (1), the exponent for the distance characteristic of the gradation value of the corrected normalized return-light image $G_2''$ can be matched with the exponent for the distance characteristic of the gradation value of the normalized fluorescence image $G_1'$.

Therefore, by storing the exponent a in the correction processing portion 19 and by raising the gradation value of the return-light image $G_2$ input thereto to the power of the exponent a, the exponent for the distance characteristic of the gradation value of the return-light image $G_2$ can substantially be matched with the exponent for the distance characteristic of the gradation value of the fluorescence image $G_1$.

As a fluorescent agent, FITC (Fluoresceinisothiocyanate), which is a fluorescent dye, combined with an antibody that binds to a receptor that is specifically expressed at a tumor-cell surface, for example, an antibody CD 44, is conceivable.

Figure 6:
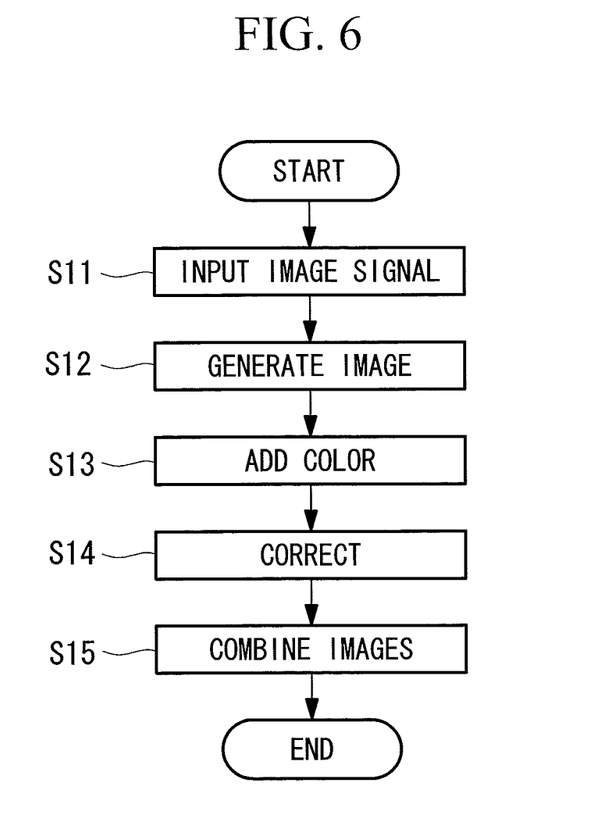
FIG. 6 is a flowchart for explaining an image processing method according to the embodiment of the present invention.

An image processing method using the thus-configured image processing device 6 according to this embodiment will be described with reference to FIG. 6.

Once the image signal S acquired by the image-acquisition element 14 is input (Input Step S11), the fluorescence image $G_1$ and the return-light image $G_2$ are generated at the image generating portion 16 (Generating Step S12), and, by inputting the generated fluorescence image $G_1$ and return-light image $G_2$ to different frame memories 18a to 18c, the color information is added thereto (Color-adding Step S13). The correction processing portion 19 applies the correction processing to the return-light image $G_2$ that has been input to the G frame memory 18b, by raising it to the power of the exponent a (Correction Step S14). Then, the fluorescence image $G_1$, which is output from the R and B frame memories 18a and 18c, and the return-light image $G_2''$, which is output from the G frame memory 18b and subjected to the correction processing at the correction processing portion 19, are combined at the image combining portion 20 (Combining Step S15) and output to the monitor 7.

The correction processing portion 19 performs the correction in which the gradation value of the return-light image $G_2$ is raised to the power of the exponent a.

The distance characteristic of the fluorescence image $G_1$ is approximated by an exponential function based on the exponent a1, and the distance characteristic of the return-light image $G_2$ is approximated by an exponential function based on the exponent a2; however, the corrected return-light image $G_2''$ and the fluorescence image $G_1$ both become an exponential function based on the exponent a1, and thus, there is a proportional relationship between the two. Therefore, even if the distance between the objective lens 13 and the observation subject A is changed, the fluorescence image $G_1$ and the corrected return-light image $G_2''$ change with a constant proportion. In other words, the combined color image has colors in a constant proportion regardless of changes in the observation distance, and thus, for example, a region of the fluorescence image $G_1$ in which the fluorescence intensity is greater (for example, a diseased portion) can be displayed constantly and continuously in the same manner.

As has been described, with the image processing device 6 and the image processing method according to this embodiment, because the proportion of the change in the fluorescence intensity depending on the observation distance matches the proportion of the change in the return-light intensity, even if the observation distance is changed, the proportion of coloration in the combined image, which is displayed by being color coded, does not change. Therefore, there is an advantage in that observation can be performed with high quantitativeness.

On the other hand, in the prior art, due to the difference in internal scattering or surface scattering, the fluorescence emitted from the subject and the reflected light returning from the subject by being reflected at the surface thereof differ in terms of the distance dependency of the amount of light acquired by a photodetector. Because of this, even when observing the same subject, if the distance between an objective lens and the subject (observation distance) is changed, the ratio of the amount of fluorescent light and the amount of the reflected light acquired by the photodetector changes, thus changing the colors.

According to the image processing device 6 and the image processing method in this embodiment, even if the observation distance is changed, the observation precision can be enhanced by reducing color changes by suppressing changes in the ratio of the amount of fluorescent light and the amount of reflected light acquired by a photodetector.

Figure 7:
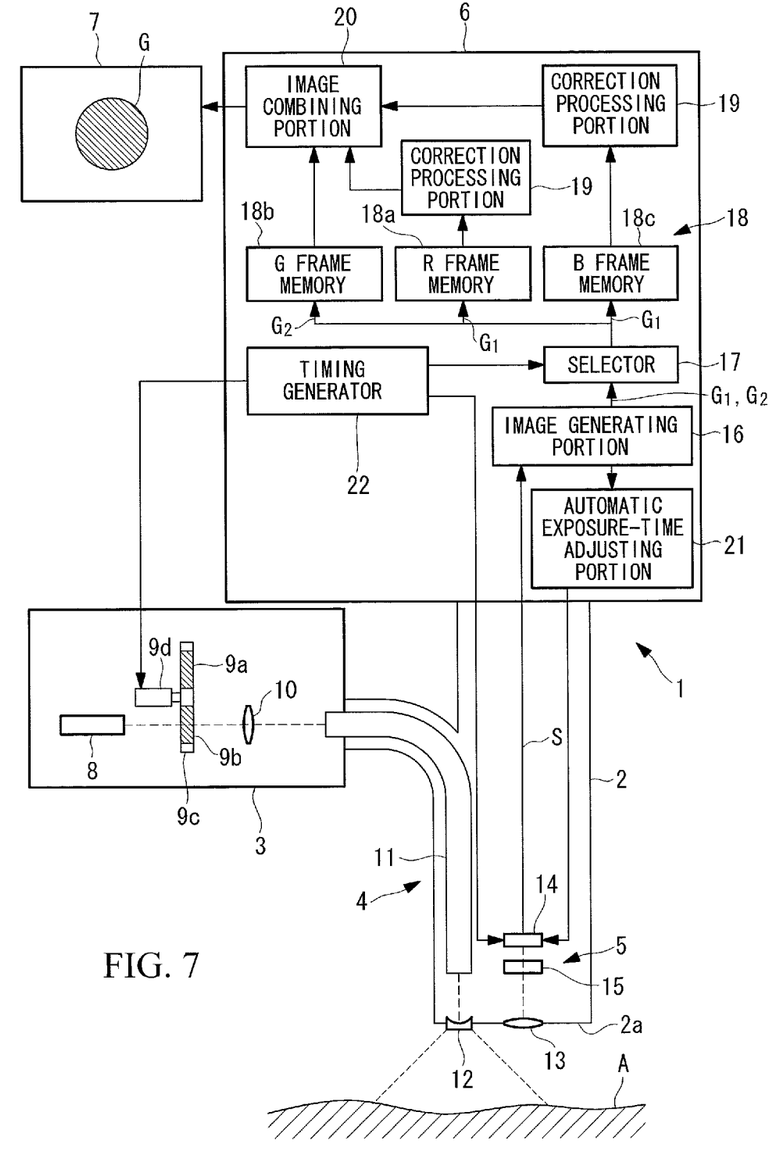
FIG. 7 is an overall configuration diagram of a modification of the endoscope device in FIG. 1.

In this embodiment, although the exponent $a=a1/a2$ is stored in the correction processing portion 19 and the input return-light image $G_2$ is input to the correction processing portion 19 to be raised to the power of the exponent a, instead of this, as shown in FIG. 7, the inverse of the exponent a, that is, $a2/a1$, may be stored in the correction processing portion 19, and the fluorescence image $G_1$ may be input to the correction processing portion 19 to be raised to the power of the exponent $a2/a1$.

Figure 8:
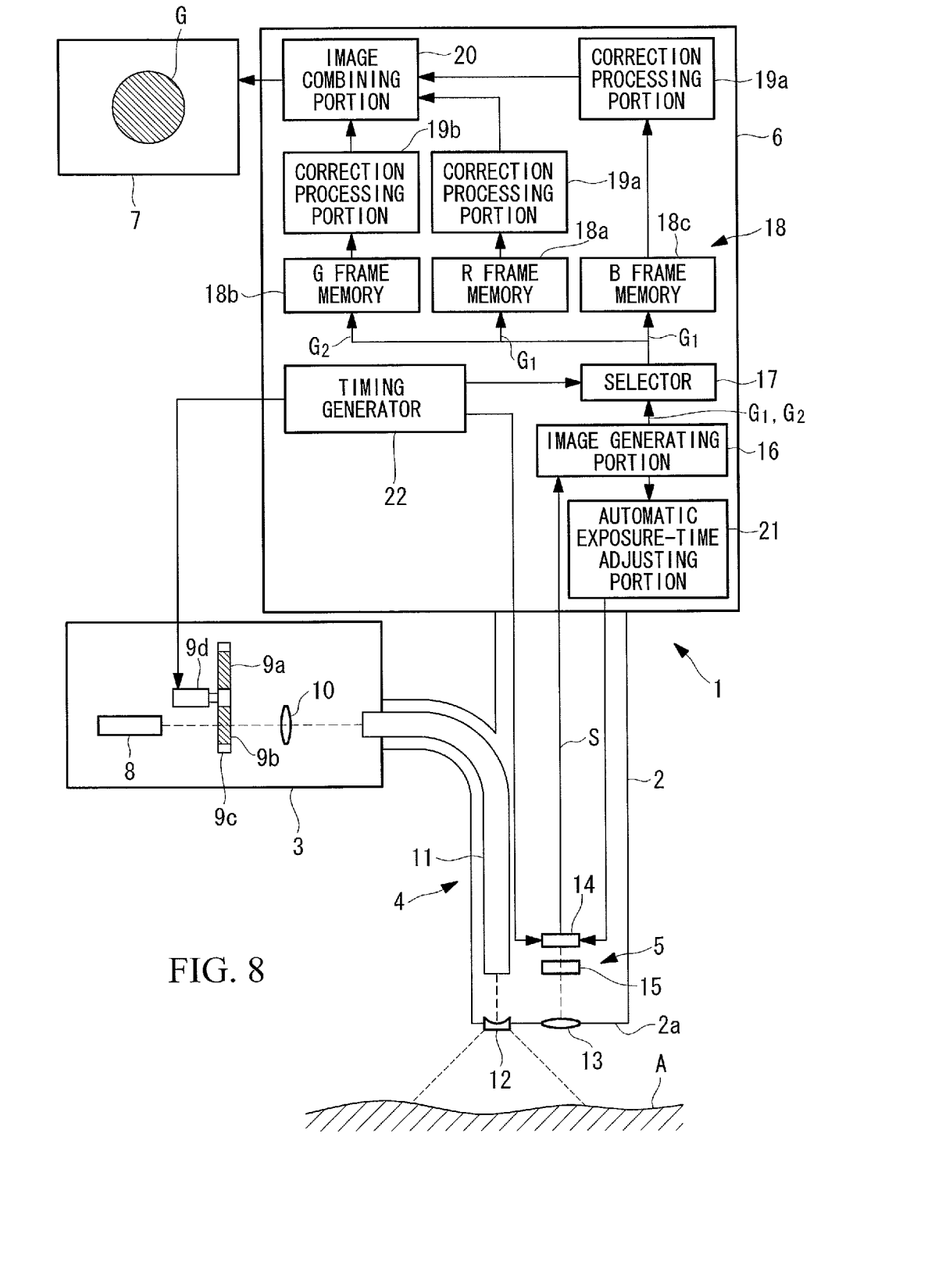
FIG. 8 is an overall configuration diagram of another modification of the endoscope device in FIG. 1.

In addition, as shown in FIG. 8, two types of correction processing portions 19a and 19b may be provided so that an exponent $1/a1$ is stored in the one correction processing portion 19a and an exponent $1/a2$ is stored in the other correction processing portion 19b. By doing so, the correction processing portion 19a raises the input fluorescence image $G_1$ to the power of the exponent $1/a1$, and the other correction processing portion 19b raises the input return-light image $G_2$ to the power of the exponent $1/a2$, which makes it possible to approximate the respective distance characteristics by linear functions. Accordingly, there is an advantage in that it is possible to establish a proportional relationship between the distance characteristic of the gradation value for the fluorescence image $G_1$ and the distance characteristic of the gradation value for the return-light image $G_2$, which prevents changes in observation results even if the observation distance is changed, and it is possible to perform highly precise observation.

Figure 9:
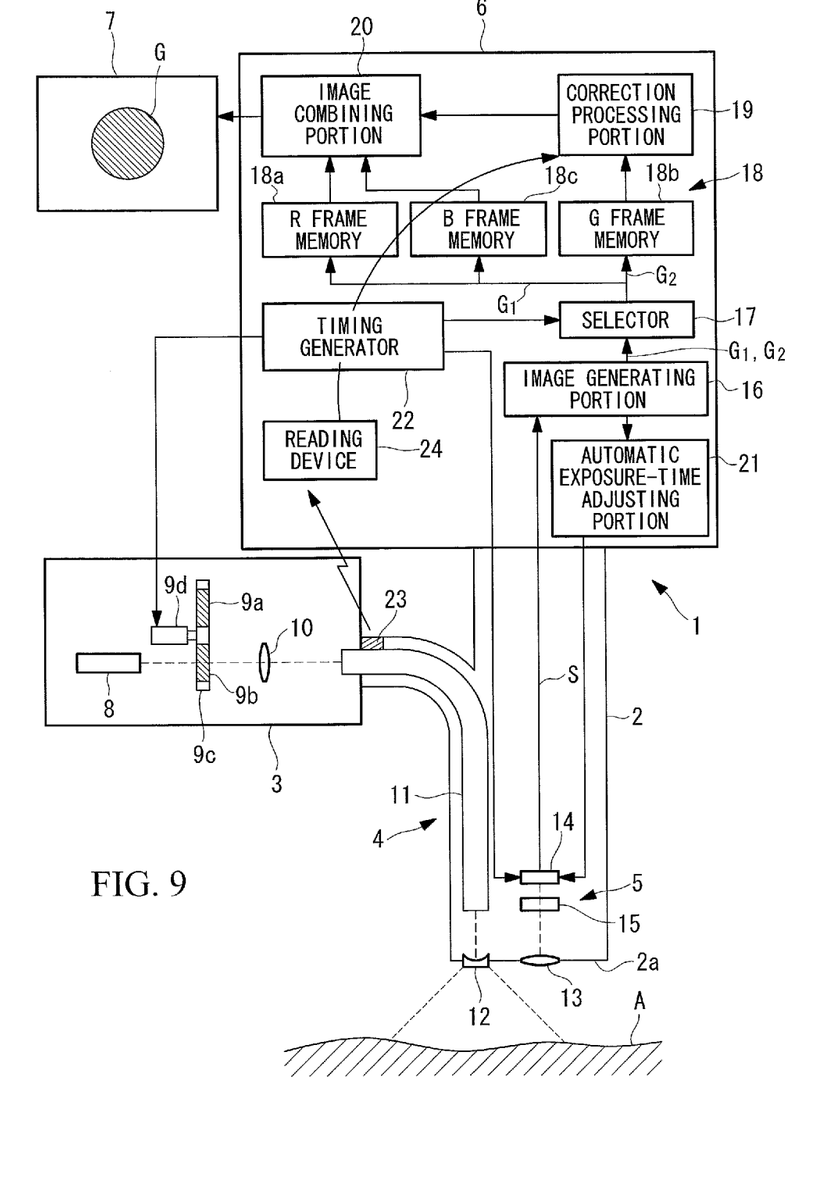
FIG. 9 is an overall configuration diagram of another modification of the endoscope device in FIG. 1.

Furthermore, although the inserted portion 2 of the endoscope device 1 is appropriately detached/attached when changing observation methods or observation conditions, in order to compensate for the differences in the distance characteristics due to the variability among inserted portions 2, as shown in FIG. 9, identification-information retaining portions 23 may be provided in the inserted portions 2, an identification-information reading portion 24 may be provided in the image processing device 6, and the identification information may be stored in the correction processing portion 19 in association with the exponents. When an inserted portion 2 is connected to the image processing device 6, the identification-information reading portion 24 reads the identification information stored in the identification-information retaining portion 23 and sends it to the correction processing portion 19, and the correction processing portion 19 compensates for the differences in the distance characteristics due to variability among the inserted portions 2 by raising the return-light image $G_2$ to the power of the exponent a that is appropriate for the identification information; thus, there is an advantage in that it is possible to perform highly precise observation even if the inserted portion 2 is exchanged.

Figure 10:
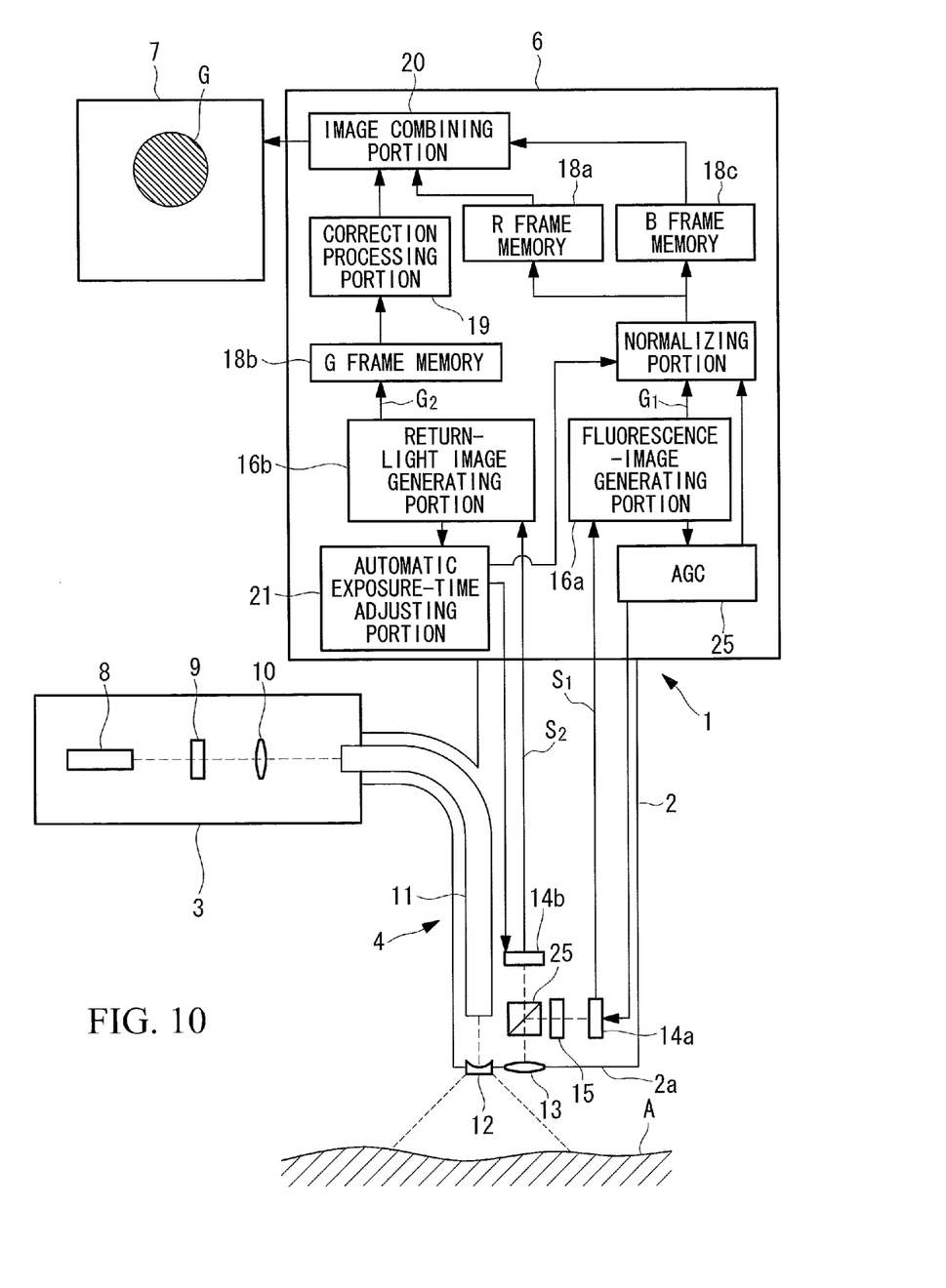
FIG. 10 is an overall configuration diagram of another modification of the endoscope device in FIG. 1.

Additionally, although the fluorescence image $G_1$ and the return-light image $G_2$ are acquired in a time-division manner by using the single image-acquisition element 14 in this embodiment, instead of this, as shown in FIG. 10, the observation subject A may be irradiated with the illumination light and the excitation light at the same time, return light returning from the observation subject A and fluorescence therefrom may be divided by a dichroic mirror 25, and they may be captured by two different image-acquisition elements 14a and 14b. Reference sign 16a indicates a fluorescence-image generating portion that generates a fluorescence image $G_1$ from an image signal $S_1$ acquired by the image-acquisition element 14a, reference sign 16b indicates a return-light image generating portion that generates a return-light image $G_2$ from an image signal $S_2$ acquired by the image-acquisition element 14b, and reference sign 9 indicates a filter that extracts excitation light (for example, 730 to 750 nm) and illumination light (630 to 650 nm).

In addition, in this embodiment, a plurality of fluorescence images $G_1$ and return-light images $G_2$ are acquired while changing the observation distance with respect to the standard specimen, and the exponent a is calculated based on the distance characteristic obtained by plotting them. Alternatively, the fluorescence image $G_1$ and the return-light image $G_2$ may be acquired at two different observation distances $d_1$ and $d_2$, respectively, and, by using their gradation values (for example, average values of gradation values for a predetermined region of interest) $G_1(d_1)$, $G_1(d_2)$, $G_2(d_1)$, and $G_2(d_2)$, the exponent a may be determined so as to satisfy Equation (2) below:

$$a=\log(G_1(d_1)/G_1(d_2))/\log(G_2(d_1)/G_2(d_2)) \qquad (2).$$

By dong so, the exponent a can directly be calculated without performing approximation calculation.

In addition, by using two standard specimens and by capturing these standard specimens, which are disposed so as to be in the same viewing field, by means of the image-acquisition element 14, the above-described exponent a can be obtained with a single image capturing.

In addition, alternatively to the automatic exposure-time adjusting portion 21 that automatically adjusts the exposure time of the image-acquisition element 14, automatic gain control (AGC) 25 for controlling the gain of the image-acquisition portion or automatic light control for automatically controlling the intensity of the radiated light from the light source portion 3 may be performed.

Additionally, instead of storing the exponents a, a1, and a2 in the correction processing portion 19 and performing the exponentiation each time, a lookup table (not shown) in which the gradation values of the fluorescence image $G_1$ and/or the return-light image $G_2$ are associated with powers obtained by raising the gradation values to the power of the exponents a, a1, and a2 may be stored, and the powers may be output in response to the gradation values of the input fluorescence image $G_1$ and/or return-light image $G_2$.

Furthermore, in addition to assigning R, G, and B primary color signals to the image signals, color assignment for regions with greater fluorescence brightness and regions with lower fluorescence brightness may be changed by employing a color matrix circuit in the image combining portion 20.

In addition, the order of the R, G, and B frame memories 18a to 18c that add the color information and the correction processing portion 19 that applies the correction processing may be switched.

A first aspect of the present invention provides an image processing device including an illuminating portion that irradiates a subject with illumination light and excitation light; a fluorescence image-acquisition portion that acquires a fluorescence image by capturing fluorescence generated at the subject due to the irradiation with the excitation light from the illuminating portion; a return-light image-acquisition portion that acquires a return-light image by capturing return light returning from the subject due to the irradiation with the illumination light from the illuminating portion; a color-image generating portion that generates a plurality of color images by adding different types of color information that constitute a color space to the fluorescence image acquired by the fluorescence image-acquisition portion and the return-light image acquired by the return-light image-acquisition portion; and an image combining portion that combines the plurality of color images generated by the color-image generating portion, wherein at least one of the fluorescence image and the return-light image is subjected to, by the color-image generating portion, correction processing in which exponents for distance characteristics, which are approximated to exponential functions, for the fluorescence image and the return-light image are matched with each other.

With the first aspect of the present invention, by irradiating the subject with the illumination light emitted from the illuminating portion, the return-light image is acquired by capturing the return light from the subject by means of the return-light image-acquisition portion, and, by irradiating the subject with the excitation light from the illuminating portion, the fluorescence image is acquired by capturing the fluorescence generated at the subject by means of the fluorescence image-acquisition portion. At the color-image generating portion, different types of color information are added to the acquired return-light image and fluorescence image, and thus, the plurality of color images are generated. Here, the generation of the plurality of color images by adding different types of color information that constitute the color space refers to, for example, assignment of the fluorescence image or the return-light image to the respective types of information about R, G, and B dimensions that constitute an RGB color space. The plurality of color images that have been generated are input to the image combining portion to be combined.

In this case, the color-image generating portion makes the exponents for distance characteristic of the fluorescence image and the return-light image match with each other by applying the correction processing to at least one of the fluorescence image and the return-light image. By doing so, with regard to an identical subject, even when the distance to the subject, at which the fluorescence image and the return-light image are captured, is changed, equivalent changes occur in the fluorescence image and the return-light image so that changes in the ratio of the color information in the color images combined at the image combining portion can be made uniform over the entire screen, thus enhancing the quantitativeness of the observation.

In the first aspect of the present invention, an R-component, a G-component, and a B-component may constitute the color information.

By doing so, a plurality of color images, to each of which different types of color information have been added, are combined, and a combined image is generated, in which a portion with a greater fluorescence intensity and a portion with a greater return-light intensity have different colors in the color space. For example, in the case in which the excitation light is radiated after adding a fluorescent agent that is specifically adsorbed at a diseased portion, the diseased portion can be displayed as a region having a greater fluorescence intensity, a combined image in which such a diseased portion has a different color can be generated, and the ease of observation can be enhanced.

In addition, with the first aspect of the present invention, the color-image generating portion may raise a gradation value of the return-light image to the power of a third exponent that is obtained by dividing a first exponent obtained by means of a power approximation for the distance characteristic of the fluorescence image by a second exponent obtained by means of a power approximation for the distance characteristic of the return-light image.

By doing so, the distance characteristic of the fluorescence image and the distance characteristic of the return-light image can be standardized as exponential functions based on the first exponent, which makes it possible to enhance the quantitativeness of observation by reducing the differences in the distance characteristics.

Here, the distance characteristic of the fluorescence image and the distance characteristic of the return-light image respectively mean the characteristic regarding the amount of the fluorescent light that is received depending on the distance to the image-acquisition portion from the subject emitting light due to the excitation light and the characteristic regarding the amount of the return light that is received depending on the distance to the image-acquisition portion from the subject illuminated by the illumination light.

In addition, with the first aspect of the present invention, the color-image generating portion may raise a gradation value of the fluorescence image to the power of a fourth exponent that is obtained by dividing a second exponent obtained by means of a power approximation for the distance characteristic of the return-light image by a first exponent obtained by means of a power approximation for the distance characteristic of the fluorescence image.

By doing so, the distance characteristic of the fluorescence image and the distance characteristic of the return-light image can be standardized as exponential functions based on the second exponent, which makes it possible to enhance the quantitativeness of observation by reducing the differences in the distance characteristics by establishing a mutually proportional relationship therebetween.

Furthermore, with the first aspect of the present invention, the color-image generating portion may raise a gradation value of the fluorescence image to the power of the inverse of a first exponent obtained by means of a power approximation for the distance characteristic of the fluorescence image and also raise a gradation value of the return-light image to the power of the inverse of a second exponent obtained by means of a power approximation for the distance characteristic of the return-light image.

By doing so, a linear function can be formed by the distance characteristic of the fluorescence image and the distance characteristic of the return-light image, a mutually proportional relationship can be established, and thus, the quantitativeness of observation can be enhanced by reducing the differences in the distance characteristics.

In addition, with the first aspect of the present invention, the color-image generating portion may raise a gradation value of the return-light image to the power of a fifth exponent such that identical values are obtained when gradation values of the fluorescence image are divided by values obtained by raising gradation values of the return-light images acquired at different distances to the power of the fifth exponent.

By doing so, the quantitativeness of observation can similarly be enhanced by reducing the differences in the distance characteristics by raising the gradation value of the return-light image to the power of the fifth exponent.

Furthermore, a second aspect of the present invention provides an image processing method including: inputting a fluorescence image obtained by capturing fluorescence generated at a subject due to irradiation with excitation light and a return-light image obtained by capturing return light returning from the subject due to irradiation with illumination light; applying correction processing by raising a gradation value of the return-light image to the power of a third exponent that is obtained by dividing a first exponent obtained by means of a power approximation for a distance characteristic of the fluorescence image by a second exponent obtained by means of a power approximation for a distance characteristic of the return-light image; generating a plurality of color images by adding different types of color information that constitute a color space to the fluorescence image and the return-light image; and combining the plurality of color images that have been subjected to the correction processing.

Additionally, a third aspect of the present invention provides an image processing method including: inputting a fluorescence image obtained by capturing fluorescence generated at a subject due to irradiation with excitation light and a return-light image obtained by capturing return light returning from the subject due to irradiation with illumination light; applying correction processing by raising a gradation value of the fluorescence image to the power of a fourth exponent that is obtained by dividing a second exponent obtained by means of a power approximation for a distance characteristic of the return-light image by a first exponent obtained by means of a power approximation for a distance characteristic of the fluorescence image; generating a plurality of color images by adding different types of color information that constitute a color space to the fluorescence image and the return-light image; and combining the plurality of color images that have been subjected to the correction processing.

Furthermore, a fourth aspect of the present invention provides an image processing method including: inputting a fluorescence image obtained by capturing fluorescence generated at a subject due to irradiation with excitation light and a return-light image obtained by capturing return light returning from the subject due to irradiation with illumination light; applying correction processing by raising a gradation value of the fluorescence image to the power of the inverse of a first exponent obtained by means of a power approximation for a distance characteristic of the fluorescence image and also by raising a gradation value of the return-light image to the power of the inverse of a second exponent obtained by means of a power approximation for a distance characteristic of the return-light image; generating a plurality of color images by adding different types of color information that constitute a color space to the fluorescence image and the return-light image; and combining the plurality of color images that have been subjected to the correction processing.

The present invention according to this embodiment affords an advantage in that, even if the observation distance is changed, a fluorescent region with a greater brightness can be displayed without a change, and thus, the quantitativeness of observation can be enhanced.

REFERENCE SIGNS LIST

A observation subject (subject)
$G_1$ fluorescence image
$G_2$ return-light image
4 illumination unit (illuminating portion)
5 image-acquisition unit (fluorescence image-acquisition portion, return-light image-acquisition portion)
6 image processing device
18 color-image generating portion
20 image combining portion

What is claimed is:

1. An image processing device comprising:
an illuminating portion that irradiates a subject with illumination light and excitation light;
a fluorescence image-acquisition portion that acquires a fluorescence image by capturing fluorescence generated at the subject due to the irradiation with the excitation light from the illuminating portion;
a return-light image-acquisition portion that acquires a return-light image by capturing return light returning from the subject due to the irradiation with the illumination light from the illuminating portion;
a color-image generating portion that generates a plurality of color images by adding different types of color information that constitute a color space to the fluorescence image acquired by the fluorescence image-acquisition portion and the return-light image acquired by the return-light image-acquisition portion; and
an image combining portion that combines the plurality of color images generated by the color-image generating portion,
wherein at least one of the fluorescence image and the return-light image is subjected to, by the color-image generating portion, correction processing in which exponents for distance characteristics, which are approximated to exponential functions, for the fluorescence image and the return-light image are matched with each other.

2. The image processing device according to claim 1, wherein an R-component, a G-component, and a B-component constitute the color information.

3. Image processing device according to claim 1, wherein the color-image generating portion raises a gradation value of the return-light image to the power of a third exponent that is obtained by dividing a first exponent obtained by means of a power approximation for the distance characteristic of the fluorescence image by a second exponent obtained by means of the power approximation for the distance characteristic of the return-light image.

4. Image processing device according to claim 1, wherein the color-image generating portion raises a gradation value of the fluorescence image to the power of a fourth exponent that is obtained by dividing a second exponent obtained by means of a power approximation for the distance characteristic of the return-light image by the first exponent obtained by means of a power approximation for the distance characteristic of the fluorescence image.

5. Image processing device according to claim 1, wherein the color-image generating portion raises a gradation value of the fluorescence image to the power of the inverse of a first exponent obtained by means of a power approximation for the distance characteristic of the fluorescence image and also raises a gradation value of the return-light image to the power of the inverse of a second exponent obtained by means of a power approximation for the distance characteristic of the return-light image.

6. Image processing device according to claim 1, wherein the color-image generating portion raises a gradation value of the return-light image to the power of a fifth exponent such that identical values are obtained when gradation values of the fluorescence image are divided by values obtained by raising gradation values of the return-light images acquired at different distances to the power of the fifth exponent.

7. An image processing method comprising:
  inputting a fluorescence image obtained by capturing fluorescence generated at a subject due to irradiation with excitation light and a return-light image obtained by capturing return light returning from the subject due to irradiation with illumination light;
  applying correction processing by raising a gradation value of the return-light image to the power of a third exponent that is obtained by dividing a first exponent obtained by means of a power approximation for a distance characteristic of the fluorescence image by a second exponent obtained by means of a power approximation for a distance characteristic of the return-light image;
  generating a plurality of color images by adding different types of color information that constitute a color space to the fluorescence image and the return-light image; and
  combining the plurality of color images that have been subjected to the correction processing.

8. An image processing method comprising:
  inputting a fluorescence image obtained by capturing fluorescence generated at a subject due to irradiation with excitation light and a return-light image obtained by capturing return light returning from the subject due to irradiation with illumination light;
  applying correction processing by raising a gradation value of the fluorescence image to the power of a fourth exponent that is obtained by dividing a second exponent obtained by means of a power approximation for a distance characteristic of the return-light image by a first exponent obtained by means of a power approximation for a distance characteristic of the fluorescence image;
  generating a plurality of color images by adding different types of color information that constitute a color space to the fluorescence image and the return-light image; and
  combining the plurality of color images that have been subjected to the correction processing.

9. An image processing method comprising:
  inputting a fluorescence image obtained by capturing fluorescence generated at a subject due to irradiation with excitation light and a return-light image obtained by capturing return light returning from the subject due to irradiation with illumination light;
  applying correction processing by raising a gradation value of the fluorescence image to the power of the inverse of a first exponent obtained by means of a power approximation for a distance characteristic of the fluorescence image and also by raising a gradation value of the return-light image to the power of the inverse of a second exponent obtained by means of a power approximation for a distance characteristic of the return-light image;
  generating a plurality of color images by adding different types of color information that constitute a color space to the fluorescence image and the return-light image; and
  combining the plurality of color images that have been subjected to the correction processing.

* * * * *